United States Patent [19]

Brunner

[11] Patent Number: 4,693,745
[45] Date of Patent: Sep. 15, 1987

[54] CYCLOHEXANEDIONECARBOXYLIC ACID DERIVATIVES WITH HERBICIDAL AND PLANT GROWTH REGULATING PROPERTIES

[75] Inventor: Hans-Georg Brunner, Lausen, Switzerland

[73] Assignee: Ciba-Geigy Corporation, Ardsley, N.Y.

[21] Appl. No.: 785,822

[22] Filed: Oct. 9, 1985

Related U.S. Application Data

[63] Continuation-in-part of Ser. No. 673,077, Nov. 19, 1984, Pat. No. 4,618,360, which is a continuation-in-part of Ser. No. 610,222, May 14, 1984, Pat. No. 4,584,013.

[30] Foreign Application Priority Data

May 18, 1983 [CH] Switzerland ............... 2693/83
Dec. 19, 1983 [CH] Switzerland ............... 6747/83

[51] Int. Cl.$^4$ ............... A01N 43/40; A01N 37/00; C07D 265/30; C07D 211/06; C07D 207/00; C07C 121/46; C07C 69/74; C07C 61/08

[52] U.S. Cl. ............... 71/94; 71/88; 71/95; 71/98; 71/105; 71/106; 71/113; 71/115; 71/118; 544/99; 544/158; 544/159; 544/162; 544/163; 544/164; 544/168; 546/226; 548/539; 556/117; 260/501.15; 560/118; 560/125; 560/126; 562/500; 562/507; 562/508; 564/123; 564/188; 564/191

[58] Field of Search ............... 562/500, 507, 508; 560/118, 125, 126; 564/188, 191, 123; 544/99, 158, 168, 162, 159, 163, 164; 546/226; 548/539; 260/501.15; 71/88, 94, 95, 98, 105, 106, 113, 115, 118; 556/117

[56] References Cited

U.S. PATENT DOCUMENTS 3,950,420  4/1976  Sawaki et al. ............... 71/106 X
3,989,737  11/1976  Sawaki et al. ............... 71/106 X

FOREIGN PATENT DOCUMENTS 2039466  2/1972  Fed. Rep. of Germany .
2232730  1/1974  Fed. Rep. of Germany .
558319  1/1975  Switzerland .

Primary Examiner—Werren B. Lone
Assistant Examiner—Vera C. Clarke
Attorney, Agent, or Firm—Edward McC. Roberts; Kevin T. Mansfield

[57] ABSTRACT

Novel cyclohexanedionecarboxylic acid derivatives have herbicidal and plant growth regulating properties. The cyclohexanedionecarboxylic acid derivatives have the formula I

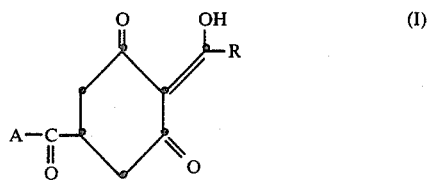

wherein
A is an —OR$_2$ or —NR$_3$R$_4$ radical,
R is C$_3$-C$_6$ cycloalkyl,
R$_2$, R$_3$ and R$_4$ are each independently hydrogen, C$_1$-C$_6$alkyl, C$_1$-C$_6$haloalkyl, C$_2$-C$_{10}$alkoxyalkyl, C$_2$-C$_{10}$alkylthioalkyl; C$_3$-C$_6$alkenyl which is unsubstituted or substituted by halogen, C$_1$-C$_4$alkoxy or C$_1$-C$_4$alkylthio; C$_3$-C$_6$alkynyl; phenyl or C$_1$-C$_6$aralkyl, wherein the phenyl nucleus is unsubstituted or substituted by halogen, C$_1$-C$_4$alkyl, C$_1$-C$_4$alkoxy, C$_1$-C$_4$haloalkyl, nitro or cyano; one of R$_3$ and R$_4$ is methoxy; or
R$_3$ and R$_4$, together with the nitrogen atom to which they are attached, form a 5- or 6-membered heterocyclic ring system which may contain an additional oxygen or sulfur atom in the ring; and the metal or ammonium salts thereof.

25 Claims, No Drawings

CYCLOHEXANEDIONECARBOXYLIC ACID DERIVATIVES WITH HERBICIDAL AND PLANT GROWTH REGULATING PROPERTIES

CROSS-REFERENCE TO RELATED APPLICATION

This is a continuation-in-part of my application Ser. No. 673,077 filed Nov. 19, 1984, now U.S. Pat. No. 4,618,360, which in turn is a continuation-in-part of my application Ser. No. 610,222 filed May 14, 1984, now U.S. Pat. No. 4,584,013.

The present invention relates to novel cyclohexanedionecarboxylic acid derivatives with herbicidal and plant growth regulating properties, to compositions which contain them, and to the use of said derivatives for selective and total weed control and for regulating plant growth.

The novel cyclohexanedionecarboxylic acid derivatives have the formula I

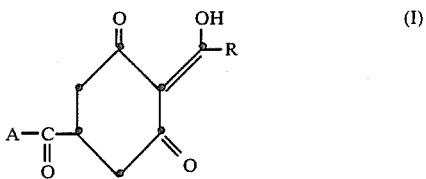

wherein
A is an $-OR_2$ or $-NR_3R_4$ radical,
R is $C_3-C_6$cycloalkyl,
$R_2$, $R_3$ and $R_4$ are each independently hydrogen, $C_1-C_6$alkyl, $C_1-C_6$haloalkyl, $C_2-C_{10}$alkoxyalkyl, $C_2-C_{10}$alkylthioalkyl; $C_3-C_6$alkenyl which is unsubstituted or substituted by halogen, $C_1-C_4$alkoxy or $C_1-C_4$alkylthio; $C_3-C_6$alkynyl; phenyl or $C_1-C_6$aralkyl, wherein the phenyl nucleus is unsubstituted or substituted by halogen, $C_1-C_4$alkyl, $C_1-C_4$alkoxy, $C_1-C_4$haloalkyl, nitro or cyano; one of $R_3$ and $R_4$ is methoxy or $R_3$ and $R_4$, together with the nitrogen atom to which they are attached, also form a 5- or 6-membered heterocyclic ring system which may contain an additional oxygen or sulfur atom in the ring or a metal or ammonium salt thereof.

In the above definitions the alkyl radicals comprise both straight chain and branched radicals, e.g. methyl, ethyl, propyl, isopropyl, butyl, isobutyl, sec-butyl, tert-butyl, as well as all stereoisomers of the higher homologues. Alkenyl and alkynyl also comprise straight chain and branched radicals, e.g. vinyl, allyl, methallyl, butenyl, methylbutenyl and dimethylbutenyl, ethynyl, propynyl, butynyl, methylbutynyl and dimethylbutynyl.

The cycloalkyl group encompasses cyclopropyl, cyclobutyl, cyclopentyl and cyclohexyl.

Halogen is fluorine, chlorine, bromine or iodine.

A 5- or 6-membered heterocyclic ring system $-NR_3R_4$ which may contain an additional oxygen or sulfur atom in the ring is pyrrole, pyrolidine, piperidine, morpholine or also thiomorpholine. These rings may also be substituted by methyl.

The salts of these compounds are obtained with bases. Suitable bases are preferably alkali metal hydroxides, alkaline earth metal hydroxides, iron, copper, nickel and zinc hydroxides, and also ammonia or quaternary $C_1-C_4$alkylammonium or $C_1-C_4$hydroxyalkylammonium bases.

The cyclohexanedionecarboxylic acid derivatives of the formula I have good herbicidal and plant growth regulating properties. Particularly effective compounds comprise the following groups:

cyclohexane derivatives of the formula I wherein A is an ester rest $-OR_2$ and the metal and ammonium salts thereof
the derivatives of the formula I, wherein A is an $-NR_3R_4$ radical and R, is as defined above, and the metal and ammonium salts thereof.

Preferred individual compounds are:
Ethyl-4-cyclopropanoyl-3,5-cyclohexanedione-1-carboxylate
ethyl-4-cyclobutanoyl-3,5-cyclohexanedione-1-carboxylate
ethyl-4-cyclopentanoyl-3,5-cyclohexanedione-1-carboxylate
ethyl-4-cyclohexanoyl-3,5-cyclohexanedione-1-carboxylate
methyl-4-cyclopropanoyl-3,5-cyclohexanedione-1-carboxylate
isopropyl-4-cyclopropanoyl-3,5-cyclohexanedione-1-carboxylate
isobutyl-4-cyclopropanoyl-3,5-cyclohexanedione-1-carboxylate
4-cyclopropanoyl-3,5-cyclohexanedione-1-carboxylate
4-cyclopropanoyl-3,5-cyclohexanedione-1-carboxylate-tri-n-butylammonium salt
4-cyclobutanoyl-3,5-cyclohexanedione-1-carboxylate
4-cyclopentanoyl-3,5-cyclohexanedione-1-carboxylate
4-cyclohexanoyl-3,5-cyclohexanedione-1-carboxylate
dimethyl-4-cyclopropanoyl-3,5-cyclohexanedione-1-carboxamide
dimethyl-4-cyclobutanoyl-3,5-cyclohexanedione-1-carboxamide
benzyl-4-cyclopropanoyl-3,5-cyclohexanedione-1-carboxamide
and the sodium, ammonium and tetramethylammonium salts thereof.

The cyclohexanedionecarboxylic acid derivatives of the formula I can be obtained in different tautomeric forms. For example, methyl 4-(cyclopropyl-1-hydroxymethylidene)-3,5-cyclohexanedione-1-carboxylate is obtained in the following forms:

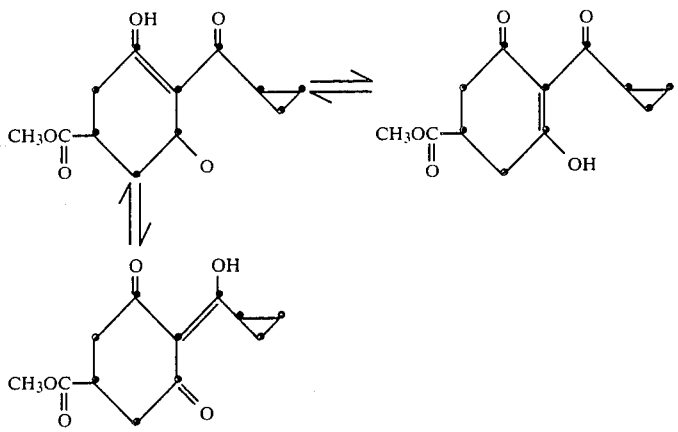

The cyclohexanedionecarboxylates of the formula I are prepared in conventional manner by reacting a 3,5-cyclohexanedionecarboxylic acid derivative of the formula II

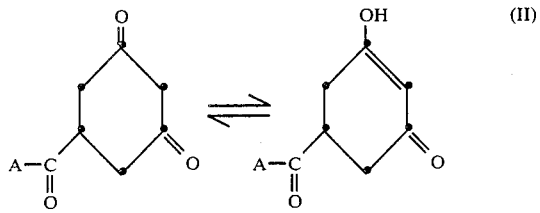

wherein A is an ester or amide radical as defined above, with a cycloalkyl-carbonic acid halide of the formula III

 (III)

wherein R is $C_3-C_6$ cycloalkyl in an inert organic solvent and in the presence of a base as acid acceptor and isolating the product so obtained.

The compounds of formula II react also with their enolic hydroxide group. This group has either to be liberated again by acid hydrolysis from the condensed —OCOR-rest or else it has to be protected previously by etherification e.g. in an acid medium in the presence of a water absorber, like concentrated sulfuric acid, distillation on a water-separated fitted preferably with a molecular sieve or with N,N-dicyclohexylcarbonimide.

The preparation of these intermediates is known e.g. from J. Am. Chem. Soc. 78 (1956) 4405 and 81 (1958) 4278 or also from the published Japanese Patent Application JA-A No. 57-47947.

Some of these intermediates are new. They correspond to the formula V

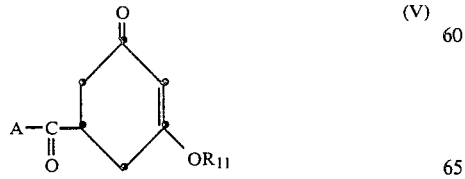

wherein A is defined as above under formula I and $R^{11}$ is selected from among $C_1-C_6$ haloalkyl, $C_3-C_6$ alkenyl, $C_3-C_6$ haloalkenyl, $C_3-C_6$ alkinyl, $C_2-C_{10}$ alkoxyalkyl and $C_2-C_{10}$ alkoxyalkenyl and are part of this invention.

Suitable solvents for these reactions are in particular aromatic hydrocarbons such as benzene, toluene and xylene, and also halogenated hydrocarbons such as chloroform, dichloroethane and carbon tetrachloride.

The reaction temperatures are in the range from room temperature to the boiling point of the reaction mixture. During the addition of acid chloride it may be necessary to cool the reaction vessel.

Suitable acid acceptors are organic and inorganic bases, e.g. pyridine, 4-aminopyridine, collidine, triethylamine, ammonium, and sodium, potassium or calcium carbonate or the corresponding bicarbonates.

Suitable acid halides of the formula III are mainly the chloride of, cycloalkanoic acids such as cyclo butyryl chloride, cyclopentanoyl chloride, cyclopropanoyl chloride or cyclohexanoyl chloride, and also the corresponding bromides.

The starting cyclohexanedionecarboxylic acid derivatives of the formula II are obtained on the one hand by hydrogenating 3,5-dihydroxybenzoic acid with hydrogen and Raney nickel and subsequently esterifying or amidating the acid radical in accordance with the following reaction scheme:

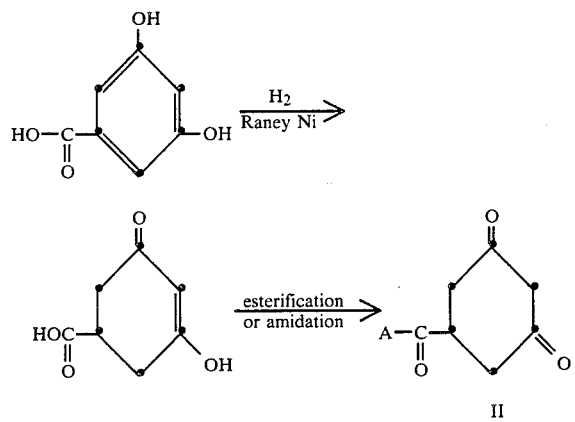

In the above reaction the keto group must be protected, e.g. as enol ether or enamine, q.v. J. Am. Chem. Soc. 78, 4405 (1956).

However, it is also possible to hydrogenate a 3,5-dihydroxybenzoic acid derivative with hydrogen and Raney nickel in accordance with the reaction scheme:

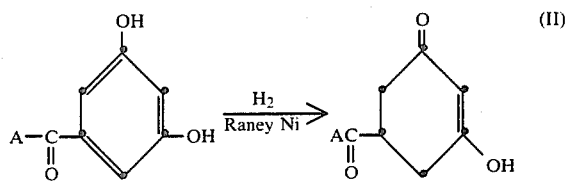

(II)

q.v. Arch. Pharm. 307, 577 (1974).

When used at low rates of application, the compounds of formula I have good growth inhibiting and selective herbicidal properties which make them most suitable for use in crops of useful plants, especially in sugar cane, cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used at very low rates of application.

In addition the compounds of formula I have pronounced growth-regulating properties which can result in an increase in the yield of cultivated plants or harvested crops. Further, many compounds of formula I have a growth inhibiting action which is dependent on the concentration. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able to promote flower formation and fruiting to a greater extent, whilst vegetative growth is inhibited.

Inhibition of the vegetative growth of monocot plants, e.g. grasses or also cultivated plants such as cereals, is sometimes desirable and advantageous. Such a growth inhibition is of economic interest, inter alia, in respect of grasses, as the frequency of cutting in flow gardens, parks, sport fields or road shoulders, can thereby be reduced. Of importance too is the inhibition of growth of herbaceous and ligneous plants on road shoulders and near transmission lines, or quite generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging. Further, the compounds of formula I are suitable for preventing stored potatoes from seeding. During winter storage, potatoes often develop sprouts which result in shrinkage, weight loss, and rot.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and docots, especially grasses, tropical cover crops and tobacco plant suckers.

The compounds of the formula I are used in unmodified form or, preferably, as compositions together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, and phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980–81.

The compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further auxiliaries such as stabilisers, antifoams, viscosity regulators, binders, tackifiers, as well as fertilisers and other compounds for obtaining special effects.

The invention is illustrated by the following Examples.

PREPARATORY EXAMPLES

Example 1: Preparation of isobutyl 4-cyclopropanoyl-3,5-cyclohexanedione-1-carboxylate

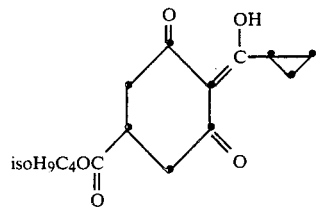

(a) Isobutyl 3,5-cyclohexanedionecarboxylate

A mixture of 50 g of 3,5-cyclohexanedione-1-carboxylic acid, 150 ml of isobutanol, 30 g of 85% orthophosphoric acid and 400 ml of toluene is boiled overnight in a water separator. The solution is then concentrated in a rotovap. The residue is taken up in 200 ml of tetrahydrofuran, and the solution is boiled for 2 hours after addition of 100 ml of 1N hydrochloric acid. The cooled solution is extracted with ethyl acetate and the organic phase is separated, washed with a saturated solution of sodium chloride, dried and concentrated. The wax-like residue is recrystallised from ether/hexane and the crystalline product melts at 74°–76° C.

(b) Isobutyl 4-cyclopropionyl-3,5-cyclohexanedione-1-carboxylate 30 ml of cyclopropanoyl chloride are added dropwise to a solution of 60 g of isobutyl 3,5-cyclohexanedionecarboxylate and 25 ml of pyridine in 400 ml of dichloroethane, and the mixture is stirred for a further 15 hours at room temperature. The reaction solution is then filtered and the filtrate is washed with 1N hydrochloric acid, dried and concentrated. The O-acylated product so obtained is taken up in 200 ml of dichloroethane, 4 g of 4-dimethylaminopyridine are added, and the reaction mixture is refluxed for 4 hours. The cooled reaction solution is then washed with 1N hydrochloric acid, dried, concentrated, and the residue is chromatographed over a small amount of silica gel, affording 51 g of isobutyl 4-cyclopropanoyl-3,5-cyclohexanedionecarboxylate as a pale oil with a refractive index of $n_D^{21}$ 1.4907.

The following compounds are prepared by procedures analogous to those described in the foregoing Examples:

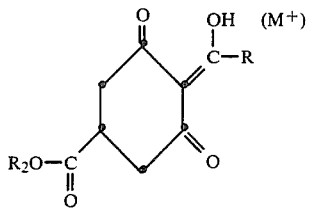

TABLE 1

| No. | OR₂ | R | Physical data |
|---|---|---|---|
| 1.01 | OC₂H₅ | cyclopropyl | $n_D^{30}$ 1.5350 |
| 1.02 | OC₂H₅ | cyclobutyl | m.p. 60–61° |
| 1.03 | OC₂H₅ | cyclopentyl | Oel |
| 1.04 | OC₂H₅ | cyclohexyl | Oel |
| 1.05 | OCH₃ | cyclopropyl | m.p. 60–64° |
| 1.06 | OCH₃ | cyclobutyl | |
| 1.07 | OCH₃ | cyclopentyl | |
| 1.08 | OCH₃ | cyclohexyl | |
| 1.09 | OC₃H₇—n | cyclopropyl | |
| 1.10 | OC₃H₇—n | cyclobutyl | |
| 1.11 | OC₃H₇—n | cyclopentyl | |
| 1.12 | OC₃H₇—n | cyclohexyl | |
| 1.13 | OC₆H₁₂—n | cyclopropyl | |
| 1.14 | OC₆H₁₂—n | cyclobutyl | |
| 1.15 | OC₆H₁₂—n | cyclopentyl | |
| 1.16 | OC₆H₁₂—n | cyclohexyl | |
| 1.17 | OC₄H₉—n | cyclopropyl | |
| 1.18 | OC₄H₉—n | cyclobutyl | |
| 1.19 | OC₄H₉—n | cyclopentyl | |
| 1.20 | OC₄H₉—n | cyclohexyl | |
| 1.21 | OCH(CH₃)₂ | cyclopropyl | m.p. 70–72° |
| 1.22 | OCH(CH₃)₂ | cyclobutyl | |
| 1.23 | OCH(CH₃)₂ | cyclopentyl | |
| 1.24 | OCH(CH₃)₂ | cyclohexyl | |
| 1.25 | OC₄H₉ iso | cyclopropyl | $n_D^{21}$ 1.4907 |
| 1.26 | OC₄H₉ iso | cyclobutyl | |
| 1.27 | OC₄H₉ iso | cyclopentyl | |
| 1.28 | OC₄H₉ iso | cyclohexyl | |
| 1.29 | OC₄H₉ tert | cyclopropyl | |
| 1.30 | OC₄H₉ tert | cyclobutyl | |
| 1.31 | OC₄H₉ tert | cyclopentyl | |
| 1.32 | OC₄H₉ tert | cyclohexyl | |
| 1.33 | OCH₂CH=CH₂ | cyclopropyl | |
| 1.34 | OCH₂CH=CH₂ | cyclobutyl | |
| 1.35 | OCH₂CH=CH₂ | cyclopentyl | |
| 1.36 | OCH₂CH=CH₂ | cyclohexyl | |
| 1.37 | OCH₂C≡CH | cyclopropyl | |
| 1.38 | OCH₂C≡CH | cyclobutyl | |
| 1.39 | OCH₂C≡CH | cyclopentyl | |
| 1.40 | OCH₂C≡CH | cyclohexyl | |
| 1.41 | OC₂H₄OCH₃ | cyclopropyl | |
| 1.42 | OC₂H₄OCH₃ | cyclobutyl | |
| 1.43 | OC₂H₄OCH₃ | cyclopentyl | |
| 1.44 | OC₂H₄OCH₃ | cyclohexyl | |
| 1.45 | OC₂H₄SCH₃ | cyclopropyl | |
| 1.46 | OC₂H₄SCH₃ | cyclobutyl | |
| 1.47 | OC₂H₄SCH₃ | cyclopentyl | |
| 1.48 | OC₂H₄SCH₃ | cyclohexyl | |
| 1.49 | benzyloxy | cyclopropyl | |
| 1.50 | benzyloxy | cyclobutyl | |
| 1.51 | benzyloxy | cyclopentyl | |
| 1.52 | benzyloxy | cyclohexyl | |
| 1.53 | OC₂H₄Cl | cyclopropyl | |
| 1.54 | OC₂H₄Cl | cyclobutyl | |
| 1.55 | OC₂H₄Cl | cyclopentyl | |
| 1.56 | OC₂H₄Cl | cyclohexyl | |
| 1.57 | OC₃H₆Cl | cyclopropyl | |
| 1.58 | OC₃H₆Cl | cyclobutyl | |
| 1.59 | OC₃H₆Cl | cyclopentyl | |
| 1.60 | OC₃H₆Cl | cyclohexyl | |
| 1.61 | OCH₂OCH₃ | cyclopropyl | |
| 1.62 | OCH₂OCH₃ | cyclobutyl | |
| 1.63 | OCH₂OCH₃ | cyclopentyl | |
| 1.64 | OCH₂OCH₃ | cyclohexyl | |
| 1.65 | OCH₃ | 1-methylcyclopropyl | |
| 1.66 | OC₂H₅ | 1-methylcyclopropyl | |
| 1.67 | OC₂H₉—n | 1-methylcyclopropyl | |
| 1.68 | OCH₂CH=CH₂ | 1-methylcyclopropyl | |
| 1.69 | benzyloxy | 1-methylcyclopropyl | |
| 1.70 | OC₂H₄OCH₃ | 1-methylcyclopropyl | |
| 1.71 | OCH₃ | 4,4-Diemthylcyclohexyl | |
| 1.72 | OC₂H₅ | 4,4-Dimethylcyclohexyl | |
| 1.73 | OC₄H₉—n | 4,4-Dimethylcyclohexyl | |
| 1.74 | OCH₂CH=CH₂ | 4,4-Diemthylcyclohexyl | |
| 1.75 | benzyloxy | 4,4-Dimethylcyclohexyl | |
| 1.76 | OC₂H₄OCH₃ | 4,4-Dimethylcyclohexyl | |
| 1.77 | OH | cyclopropyl | m.p. 142–146° |
| 1.78 | OH | cyclobutyl | |
| 1.79 | OH | cyclopentyl | m.p. 95–103° |
| 1.80 | OH | cyclohexyl | m.p. 155–158° |
| 1.81 | OH | cyclopropyl | tri-n-butylammonium salt, oil |

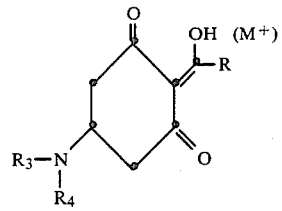

TABLE 2

| No. | NR₃R₄ | R | Physical data |
|---|---|---|---|
| 2.01 | NH₂ | cyclopropyl | |
| 2.02 | NH₂ | cyclobutyl | |
| 2.03 | NH₂ | cyclopentyl | |
| 2.04 | NH₂ | cyclohexyl | |
| 2.05 | NHCH₃ | cyclopropyl | |
| 2.06 | NHCH₃ | cyclobutyl | |
| 2.07 | NHCH₃ | cyclopentyl | |
| 2.08 | NHCH₃ | cyclohexyl | |
| 2.09 | N(CH₃)₂ | cyclopropyl | m.p. 109–112° |
| 2.10 | N(CH₃)₂ | cyclobutyl | m.p. 72–78° |
| 2.11 | N(CH₃)₂ | cyclopentyl | |
| 2.12 | N(CH₃)₂ | cyclohexyl | |
| 2.13 | N(CH₃)OCH₃ | cyclopropyl | |
| 2.14 | N(CH₃)OCH₃ | cyclobutyl | |
| 2.15 | N(CH₃)OCH₃ | cyclopentyl | |
| 2.16 | N(CH₃)OCH₃ | cyclohexyl | |
| 2.17 | NHCH₂CH=CH₂ | cyclopropyl | |
| 2.18 | NHCH₂CH=CH₂ | cyclobutyl | |
| 2.19 | NHCH₂CH=CH₂ | cyclopentyl | |
| 2.20 | NHCH₂CH=CH₂ | cyclohexyl | |
| 2.21 | N(CH₂CH=CH₂)₂ | cyclopropyl | |

TABLE 2-continued

| No. | NR₃R₄ | R | Physical data |
|---|---|---|---|
| 2.22 | N(CH₂CH=CH₂)₂ | cyclobutyl | |
| 2.23 | N(CH₂CH=CH₂)₂ | cyclopentyl | |
| 2.24 | N(CH₂CH=CH₂)₂ | cyclohexyl | |
| 2.25 | N(CH₃)C₂H₅ | cyclopropyl | |
| 2.26 | N(CH₃)C₂H₅ | cyclobutyl | |
| 2.27 | N(CH₃)C₂H₅ | cyclopentyl | |
| 2.28 | N(CH₃)C₂H₅ | cyclohexyl | |
| 2.29 | benzylamino | cyclopropyl | m.p. 130-144° |
| 2.30 | benzylamino | cyclobutyl | |
| 2.31 | benzylamino | cyclopentyl | |
| 2.32 | benzylamino | cyclohexyl | |
| 2.33 | anilino | cyclopropyl | |
| 2.34 | anilino | cyclobutyl | |
| 2.35 | anilino | cyclopentyl | |
| 2.36 | anilino | cyclohexyl | |
| 2.37 | 4-chloranilino | cyclopropyl | |
| 2.38 | 4-chloranilino | cyclobutyl | |
| 2.39 | 4-chloranilino | cyclopentyl | |
| 2.40 | 4-chloranilino | cyclohexyl | |
| 2.41 | 3-trifluormethyl-anilino | cyclopropyl | |
| 2.42 | 3-trifluormethyl-anilino | cyclobutyl | |
| 2.43 | 3-trifluormethyl-anilino | cyclopentyl | |
| 2.44 | 3-trifluormethyl-anilino | cyclohexyl | |
| 2.45 | 4-methoxyanilino | cyclopropyl | |
| 2.46 | 4-methoxyanilino | cyclobutyl | |
| 2.47 | 4-methoxyanilino | cyclopentyl | |
| 2.48 | 4-methoxyanilino | cyclohexyl | |
| 2.49 | pyrrolinyl | cyclopropyl | |
| 2.50 | pyrrolinyl | cyclobutyl | |
| 2.51 | pyrrolinyl | cyclopentyl | |
| 2.52 | pyrrolinyl | cyclohexyl | |
| 2.53 | cyclopropylamino | cyclopropyl | |
| 2.54 | cyclopropylamino | cyclobutyl | |
| 2.55 | cyclopropylamino | cyclopentyl | |
| 2.56 | cyclopropylamino | cyclohexyl | |
| 2.57 | NHC₆H₁₃n | 1-methylcyclopropyl | |
| 2.58 | NHC₂H₄SCH₃ | 4,4-dimethylcyclohexyl | |
| 2.59 | N—methylbenzyl-amino | 4,4-dimethylcyclohexyl | |
| 2.60 | anilino | 1-methylcyclopropyl | |
| 2.61 | NHC₆H₁₃n | 1-methylcyclopropyl | |
| 2.62 | NHC₂H₄SCH₃ | 3,5-dimethylcyclohexyl | |

In Example 1a, there is prepared an intermediate product. According to this example the following compounds are prepared

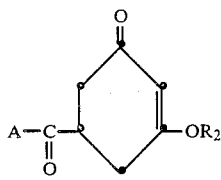

TABLE 3

| No. | A | R₂ | Physical data |
|---|---|---|---|
| 3.01 | N(CH₃)₂ | CH₃ | oil |
| 3.02 | N(CH₃)₂ | H | m.p. 152-155° |
| 3.03 | benzoyloxy | H | |
| 3.04 | 4-chlorobenzyloxy | H | |
| 3.05 | CH₃OC₂H₄O | H | |
| 3.06 | 4-benzylamino | H | |
| 3.07 | anilino | H | |
| 3.08 | anilino | CH₃ | |
| 3.09 | (CH₃)₂CHCH₂— | CH₃ | oil |

TABLE 3-continued

| No. | A | R₂ | Physical data |
|---|---|---|---|
| 3.10 | (CH₃)₂CHCH₂NH | H | |
| 3.11 | (C₂H₅)₂N | H | oil |
| 3.12 | 1-methylanilino | CH₃ | |
| 3.13 | 1-methylanilino | H | m.p. 143-145° |
| 3.14 | (CH₂=CHCH₂)₂N | CH₃ | oil |
| 3.15 | (CH₂=CHCH₂)₂N | H | resin |
| 3.16 | piperidino | CH₃ | |
| 3.17 | piperidino | H | |
| 3.18 | CH₃SC₂H₄NH | CH₃ | |
| 3.19 | CH₃SC₂H₄NH | H | resin |
| 3.20 | HSC₂H₄NH | CH₃ | wax |
| 3.21 | HSC₂H₄NH | H | |
| 3.22 | H₅C₃(CH₃)CHO | H | m.p. 76-78° |

Example 2

Formulation Examples for compounds of the formula I or mixtures thereof with herbicides

| (a) Wettable powders | (a) | (b) | (c) |
|---|---|---|---|
| Compound of Table 1 or 2 | 20% | 60% | 0.5% |
| sodium lignosulfonate | 5% | 5% | 5% |
| sodium laurylsulfate | 3% | — | — |
| sodium diisobutylnaphahalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of Table 1 or 2 | 10% | 1% |
| octylphenol polyethylene glycol ether (4-5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of Table 1 or 2 | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of Table 1 or 2 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of Table 1 or 2 | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of Table 1 or 2 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of Table 1 or 2 | 5% |
| isopropylamine | 1% |
| octylphenol polyethylene glycol ether (78 moles of ethylene oxide) | 3% |
| water | 91% |

Example 3: Preemergence herbicidal activity

Plant seeds are sown in flower pots (diameter 11 cm) in a greenhouse. Immediately afterwards the surface of the soil is treated with an aqueous emulsion of the test compound at a concentration of 4 kg a.i. per hectare. The pots are then kept in the greenhouse at a temperature of 22°–25° C. and 50 to 70% relative humidity. The test is evaluated 3 weeks later by assessing the condtions of plants. The tested compounds of Tables 1 and 2 damage most of the test plants.

Example 4: Postemergence herbicidal activity

Different cultivated plants and weeds are reared from seeds in pots in a greenhouse until they have reached the 4- to 6-leaf stage. The plants are sprayed with an aqueous emulsion of test compound (prepared from a 25% emulsifiable concentrate) at a concentration of 4 kg/ha. The treated plants are then kept under optimum conditions of light, regular watering, temperature (22°–25° C.), and relative humidity (50–70%). The test is evaluated 15 days. The tested compound of Tables 1 and 2 damage most of the plants.

Example 5: Growth inhibition of tropical cover crops

Cuttings from the test plants *Phosphocarpus palustris* and *Centrosema pubescens* are reared in plastic pots that are filled with a 1:3 earth-peat mixture. When the plants grow roots they are replanted into pots of 11 cm diameter and watered as necessary.

The test plants are kept at 70% relative humidity and 6000 lux artificial light for 14 hours per day, at day temperatures of 27° C. and night temperatures of 21° C. The fully grown test plants are cut back to a height of 15 cm. The plants are sprayed 7 days later with an aqueous emulsion or suspension of the test compounds. The test is evaluated 4 weeks after the treatment and the new growth is measured and compared to that of untreated plants which have been cut back the same day.

The results are as follows:

| | | new growth | | | |
|---|---|---|---|---|---|
| | amount | Phosphocarpus | | Centrosema | |
| compound | applied | weight | length | weight | length |
| 1.01 | 300 g/ha | 87% | 100% | 87% | 100% |
| | 1000 g/ha | 74% | 100% | 61% | 20% |
| | 3000 g/ha | 32% | 20% | 61% | 10% |
| 1.02 | 300 g/ha | 90% | 100% | 87% | 100% |
| | 1000 g/ha | 71% | 80% | 74% | 90% |
| | 3000 g/ha | 52% | 30% | 65% | 10% |
| none control | — | 100% | 100% | 100% | 100% |

Example 6: Growth regulation of soybeans

Soybeans of the "Williams" variety are sown in plastic containers (20×20 cm) in an earth/peat/sand mixture (6:3:1). The containers are put into a climatic chamber and the plants develop to the beginning of the flowering stage after about 7 weeks by optimum control of temperature, light, fertiliser addition, and watering. The plants are then sprayed with an aqueous mixture of a compound to be tested until thoroughly wetted. The rate of application corresponds to 1000 g of active ingredient and 500 l of water per hectare. Evaluation is made about 4 weeks after application.

The quantitative growth after application of the test-substance and the yield giving criteria are compared with those of not treated control plants. The substances clearly reduce the linear growth without diminishing the yield. They markedly increase the number and weight of the harvested siliques on the leading shoot.

The results for compound 1.01, which was applied at 1000 g/ha are as follows (compared with those of not treated plants=100%)

| height of plant | 82% |
|---|---|
| linear growth after applications | 46% |
| siliques on secondary shoots number | 87% |
| siliques on secondary shoots weight | 88% |
| siliques on main shoot number | 106% |
| siliques on main shoot weight | 103% |
| phytotoxic symptoms on treated plant | none |
| phytotoxic symptoms on new growth (after treatment) | none | other results were as follows:

| | | growth after treatment | | |
|---|---|---|---|---|
| compound | application rate | length % | weight % | rate % length / % weight |
| 1.01 | 1000 g/ha | 46 | 91 | 1.97 |
| 1.05 | 500 g/ha | 100 | 95 | 1.05 |
| | 1300 g/ha | 97 | 57 | 1.70 |
| 1.21 | 500 g/ha | 97 | 78 | 1.24 |
| | 1500 g/ha | 94 | 72 | 1.31 |
| 1.77 | 500 g/ha | 100 | 95 | 1.05 |
| | 1500 g/ha | 89 | 33 | 2.70 |
| 1.79 | 500 g/ha | 100 | 63 | 1.59 |

-continued

| compound | application rate | growth after treatment | | rate % length / % weight |
|---|---|---|---|---|
| | | length % | weight % | |
| | 1500 g/ha | 80 | 21 | 3.81 |
| 1.80 | 500 g/ha | 95 | 79 | 1.20 |
| | 1500 g/ha | 98 | 42 | 2.33 |
| 1.81 | 500 g/ha | 100 | 90 | 1.11 |
| | 1500 g/ha | 92 | 62 | 1.48 |
| control | — | 100 | 100 | 1.00 |

Example 7: Growth inhibition of cereals

Summer barley (*Hordeum vulgare*) and summer wheat (Triticum) are sown in sterilised soil in plastic beakers in a greenhouse and watered as required. The cereal shoots are treated about 21 days after sowing with an aqueous spray mixture of a compound of the formula I. The concentration corresponds to 3 kg of active ingredient per hectare. Evaluation of the growth of the cereals is made 28 days after application. A comparison with untreated controls shows that the growth of cereal plants treated with the test compounds is significantly reduced (controls=100%) and that the diameter of the stalks has in some cases increased. The inhibition of the linear growth is without great influence of the weight of the plant. The plant is small and sturdy and less apt for laying down because of rain and wind.

The results are as follows:

| | | barley | | | wheat | | |
|---|---|---|---|---|---|---|---|
| compound | application rate | circumference stalk | dry weight of shoot | new growth after treatment | circumference stalk | dry weight of shoot | new growth after treatment |
| 1.01 | 300 g/ha | 106 | 83 | 72 | 92 | 88 | 82 |
| | 1000 g/ha | 110 | 65 | 45 | 104 | 70 | 47 |
| | 3000 g/ha | 144 | 63 | 17 | 112 | 66 | 8 |
| 1.02 | 300 g/ha | 115 | 93 | 74 | 106 | 96 | 97 |
| | 1000 g/ha | 97 | 69 | 68 | 100 | 85 | 88 |
| | 3000 g/ha | 120 | 59 | 26 | 98 | 69 | 38 |
| 1.03 | 300 g/ha | 106 | 86 | 94 | 105 | 106 | 96 |
| | 1000 g/ha | 104 | 84 | 89 | 95 | 92 | 75 |
| | 3000 g/ha | 110 | 64 | 34 | 107 | 69 | 36 |
| 1.04 | 300 g/ha | 97 | 84 | 94 | 100 | 102 | 93 |
| | 1000 g/ha | 103 | 64 | 94 | 102 | 80 | 82 |
| | 3000 g/ha | 109 | 92 | 70 | 96 | 89 | 54 |
| 1.05 | 300 g/ha | 100 | 82 | 78 | 109 | 100 | 84 |
| | 1000 g/ha | 114 | 66 | 53 | 109 | 84 | 58 |
| | 3000 g/ha | 129 | 57 | 2 | 130 | 64 | 6 |
| 1.77 | 300 g/ha | 89 | 72 | 60 | 107 | 82 | 45 |
| | 1000 g/ha | 125 | 53 | 16 | 116 | 73 | 16 |
| | 3000 g/ha | 118 | 64 | 4 | 147 | 66 | 0 |
| 1.80 | 300 g/ha | 106 | 88 | 79 | 96 | 77 | 72 |
| | 1000 g/ha | 123 | 79 | 55 | 100 | 77 | 52 |
| | 3000 g/ha | 137 | 56 | 9 | 132 | 68 | 7 |
| control | — | 100 | 100 | 100 | 100 | 100 | 100 |

Example 8: Growth inhibition of grasses and clover

Seeds of the grasses *Lolium perenne, Poa pratensis, Festuca rubra, Festuca ovina Dactylis glomerata Cynosurus cristatus, Agropyron repens, Bromus inermis* and of two kinds of clover are sown in plastic dishes filled with an earth/peat/sand mixture (6:3:1), in a greenhouse, and watered as required. The emergent grasses are cut back weekly to a height of 4 cm, for about 6 weeks after sowing. 1 day after the last cut, the grass-mixture is sprayed with an aqueous spray of a compound to be tested. The concentration of test compound corresponds to a rate of application of 0.3 to 3 kg per hectare. The growth of the grasses is evaluated 21 days after application. The new growth is compared with that of untreated controls (100%).

The results are as follows:

| | application rate | | |
|---|---|---|---|
| compound | 300 g/ha | 1000 g/ha | 3000 g/ha |
| 1.01 | 77% | 37% | 31% |
| 1.02 | 74% | 51% | 43% |
| 1.03 | 66% | 66% | 41% |
| 1.04 | 79% | 76% | 66% |
| 1.05 | 88% | 67% | 36% |
| 1.21 | 80% | 51% | 29% |
| 1.77 | 76% | 61% | 45% |
| 1.79 | 74% | 59% | 35% |
| 1.80 | 82% | 62% | 65% |
| 1.81 | 81% | 50% | 42% |
| control | 100% | 100% | 100% |

Example 9

Growth-inhibiting test in the greenhouse. Plants of oats (*avena sativa*), *Setaria italica, Lolium perenne*, tomatoe (*solanum lycopersicum*) *Sinapsis alba Steallaria media* and beans (*Phaseolus vulgaris*) were raised in plastic pots of 12 cm diameter in the greenhouse. Two weeks, after sowing the plantlets were sprayed with the diluted concentrate of the substance to be tested in an amount that corresponds to 4 kg of active substance per hectare. One set of plants was left untreated to serve as control. The test was evaluated two weeks after application of the test substance. The length of the growth since application was measured and calculated in % of that of the untreated control plants (=100% growth).

The results are as follows:

| compound | untreated control | 2.09 | 2.10 |
|---|---|---|---|
| plants | % growth since application of test compound | | |
| *Avena sativa* | 100 | 63 | 38 |
| *Setaria italica* | 100 | 63 | 38 |
| *Lolium perenne* | 100 | 87 | 87 |
| *Solanum lycopersicum* | 100 | 38 | 63 |
| *Sinapsis alba* | 100 | 38 | 63 |
| *Stellaria media* | 100 | 63 | 38 |

-continued

| compound | untreated control | 2.09 | 2.10 |
|---|---|---|---|
| *Phaseolus vulgaris* | 100 | 13 | 100 |

What is claimed is:

1. A cyclohexanedionecarboxylic acid derivative of the formula I

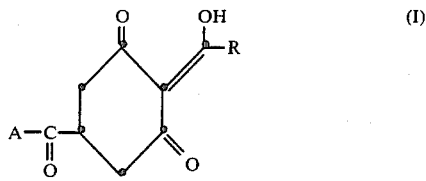

wherein
A is an —$OR_2$ or —$NR_3R_4$ radical,
R is $C_3-C_6$cycloalkyl,
$R_2$, $R_3$ and $R_4$ are each independently hydrogen, $C_1-C_6$alkyl, $C_1-C_6$haloalkyl, $C_1-C_{10}$alkoxyalkyl, $C_2-C_{10}$alkylthioalkyl; $C_3-C_6$alkenyl which is unsubstituted or substituted by halogen, $C_1-C_4$alkoxy or $C_1-C_4$alkylthio; $C_3-C_6$alkynyl; phenyl or $C_1-C_6$aralkyl, wherein the phenyl nucleus is unsubstituted or substituted by halogen, $C_1-C_4$alkyl, $C_1-C_4$alkoxy, $C_1-C_4$haloalkyl, nitro or cyano; one of $R_3$ and $R_4$ is methoxy; or
$R_3$ and $R_4$, together with the nitrogen atom to which they are attached, form a 5- or 6-membered heterocyclic ring system which may contain an additional oxygen or sulfur atom in the ring; and the metal or ammonium salts thereof.

2. A cyclohexanedionecarboxylic acid derivative according to claim 1, wherein A is an $OR_2$ radical, R is $C_3-C_6$cycloalkyl and $R_2$ is hydrogen, $C_1-C_6$alkyl, $C_1-C_6$haloalkyl, $C_2-C_{10}$alkoxyalkyl, $C_2-C_{10}$alkylthioalkyl; $C_3-C_6$alkenyl, which is unsubstituted or substituted by halogen, $C_1-C_4$alkoxy or $C_1-C_4$alkylthio; $C_3-C_6$alkynyl; phenyl or $C_1-C_6$aralkyl, wherein the phenyl nucleus is unsubstituted, or substituted by halogen, $C_1-C_4$alkyl, $C_1-C_4$alkoxy, $C_1-C_4$haloalkyl, nitro or cyano.

3. A cyclohexanedioncarboxylic acid derivative according to claim 1, wherein A is an —$NR_3R_4$ radical, R is $C_3-C_6$cycloalkyl, and $R_3$ and $R_4$ are each independently hydrogen, $C_1-C_6$alkyl, $C_1-C_6$haloalkyl, $C_2-C_{10}$alkoxyalkyl, $C_2-C_{10}$alkylthioalkyl; $C_3-C_6$alkenyl, which is unsubstituted or substituted by halogen, $C_1-C_4$alkoxy or $C_1-C_4$alkylthio; $C_3-C_6$alkynyl, phenyl or $C_1-C_6$aralkyl, wherein the phenyl nucleus is unsubstituted or substituted by halogen, $C_1-C_4$alkyl, $C_1-C_4$alkoxy, $C_1-C_4$haloalkyl nitro or cyano; one of $R_3$ and $R_4$ is methoxy; or $R_3$ and $R_4$, together with the nitrogen atom, to which they are attached, form a 5- or 6-membered heterocyclic ring system, which may contain an additional oxygen or sulfur atom in the ring.

4. Ethyl-4-cyclopropanoyl-3,5-cyclohexanedione-1-carboxylate, according to claim 1.

5. Ethyl-4-cyclobutanoyl-3,5-cyclohexanedione-1-carboxylate, according to claim 1.

6. Ethyl-4-cyclopentanoyl-3,5-cyclohexanedione-1-carboxylate, according to claim 1.

7. Ethyl-4-cyclohexanoyl-3,5-cyclohexanedione-1-carboxylate, according to claim 1.

8. Methyl-4-cyclopropanoyl-3,5-cyclohexanedione-1-carboxylate, according to claim 1.

9. Isopropyl-4-cyclopropanoyl-3,5-cyclohexanedione-1-carboxylate, according to claim 1.

10. Isobutyl-4-cyclopropanoyl-3,5-cyclohexanedione-1-carboxylate, according to claim 1.

11. 4-Cyclopropanoyl-3,5-cyclohexanedione-1-carboxylate, according to claim 1.

12. 4-Cyclopropanoyl-3,5-cyclohexanedione-1-carboxylate-tri-n-butylammonium salt, according to claim 1.

13. 4-Cyclobutanoyl-3,5-cyclohexanedione-1-carboxylate, according to claim 1.

14. 4-Cyclopentanoyl-3,5-cyclohexanedione-1-carboxylate, according to claim 1.

15. 4-Cyclohexanoyl-3,5-cyclohexanedione-1-carboxylate, according to claim 1.

16. Dimethyl-4-cyclopropanoyl-3,5-cyclohexanedione-1-carboxamide, according to claim 1.

17. Dimethyl-4-cyclobutanoyl-3,5-cyclohexanedione-1-carboxamide, according to claim 1.

18. Benzyl-4-cyclopropanoyl-3,5-cyclohexanedione-1-carboxamide, according to claim 1.

19. A composition, which contains as active ingredient a herbicidal and plant-growth regulating effective amount of a cyclohexanedionecarboxylic acid derivative according to claim 1, together with an inert carrier and/or other inert formulation assistants.

20. A method of selectively controlling weeds pre- or postemergence in crops of useful plants, which comprises applying to said useful plants or to the locus thereof an effective amount of a cyclohexanedionecarboxylic acid derivative of the formula I

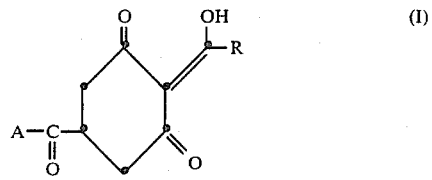

wherein
A is an —$OR_2$ or —$NR_3R_4$ radical,
R is $C_3-C_6$cycloalkyl.
$R_2$, $R_3$ and $R_4$ are each independently hydrogen, $C_1-C_6$alkyl, $C_1-C_6$haloalkyl, $C_2-C_{10}$alkoxyalkyl, $C_2-C_{10}$alkylthioalkyl; $C_3-C_6$alkenyl which is unsubstituted or substituted by halogen, $C_1-C_4$alkoxy or $C_1-C_4$alkylthio; $C_3-C_6$alkynyl; phenyl or $C_1-C_6$aralkyl, wherein the phenyl nucleus is unsubstituted or substituted by halogen, $C_1-C_4$alkyl, $C_1-C_4$alkoxy, $C_1-C_4$haloalkyl, nitro or cyano; one of $R_3$ and $R_4$ is methoxy; or
$R_3$ and $R_4$, together with the nitrogen atom to which they are attached, form a 5- or 6-membered heterocyclic ring system which may contain an additional oxygen or sulfur atom in the ring; and the metal or ammonium salts thereof.

21. The method of claim 20 wherein the weeds are grasses.

22. The method of claim 20 wherein the crops of useful plants are sugar cane, cereals, maize, soya beans, rice and cotton.

23. A method of regulating growth of useful crops plants, which comprises treating said plants, parts of plants or seeds with an effective amount of a cyclohexanedionecarboxylic acid derivative of the formula I

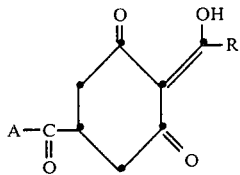

wherein
A is an —OR$_2$ or —NR$_3$R$_4$ radical,
R is C$_3$-C$_6$cycloalkyl,
R$_2$, R$_3$ and R$_4$ are each independently hydrogen, C$_1$-C$_6$alkyl, C$_1$-C$_6$haloalkyl, C$_2$-C$_{10}$alkoxyalkyl, C$_2$-C$_{10}$alkylthioalkyl; C$_3$-C$_6$alkenyl which is unsubstituted or substituted by halogen, C$_1$-C$_4$alkoxy or C$_1$-C$_4$alkylthio; C$_3$-C$_6$alkynyl; phenyl or C$_1$-C$_6$aralkyl, wherein the phenyl nucleus is unsubstituted or substituted by halogen, C$_1$-C$_4$alkyl, C$_1$-C$_4$alkoxy, C$_1$-C$_4$haloalkyl, nitro or cyano; one of R$_3$ and R$_4$ is methoxy; or
R$_3$ and R$_4$, together with the nitrogen atom to which they are attached, form a 5- or 6-membered heterocyclic ring system which may contain an additional oxygen or sulfur atom in the ring; and the metal or ammonium salts thereof.

24. A method of regulating plant growth of cereals and soybeans to obtain an increase in yield, which comprises applying to said plants an effective amount of a cyclohexanedionecarboxylic acid derivative of the formula I according to claim 23, or of a composition containing said derivative.

25. A method of claim 23 of inhibiting plant growth beyond the 2-leaf stage of tropical cover plants, which comprises applying to said plants an effective amount of the cyclohexanedionecarboxylic acid derivative or of a composition containing said derivative.

* * * * *